(12) United States Patent
Pabst et al.

(10) Patent No.: US 9,259,328 B2
(45) Date of Patent: Feb. 16, 2016

(54) EXPANDABLE CAGE FOR THE INTERBODY FUSION OF LUMBAR VERTEBRAE

(71) Applicant: spontech spine intelligence AG, Stuttgart (DE)

(72) Inventors: Martin Pabst, Donaueschingen (DE); Lino Taddia, Stockach (DE); Thomas Pandorf, Wernau (DE); Marcus Spitsenberg, Mössingen (DE); Christoph Kohlbrenner, Hersischried (DE)

(73) Assignee: spontech spine intelligence AG, Stuttgart (DE)

( * ) Notice: Subject to any disclaimer, the term of this patent is extended or adjusted under 35 U.S.C. 154(b) by 166 days.

(21) Appl. No.: 14/087,860

(22) Filed: Nov. 22, 2013

(65) Prior Publication Data

US 2014/0156007 A1    Jun. 5, 2014

(30) Foreign Application Priority Data

Nov. 26, 2012   (DE) .......................... 10 2012 023 042

(51) Int. Cl.
| | | |
|---|---|---|
| A61F 2/44 | (2006.01) | |
| A61F 2/46 | (2006.01) | |
| A61F 2/30 | (2006.01) | |

(52) U.S. Cl.
CPC . *A61F 2/447* (2013.01); *A61F 2/44* (2013.01); *A61F 2/442* (2013.01); *A61F 2/4455* (2013.01); *A61F 2/4611* (2013.01); *A61F 2002/3039* (2013.01); *A61F 2002/30151* (2013.01); *A61F 2002/30153* (2013.01); *A61F 2002/30158* (2013.01); *A61F 2002/30166* (2013.01); *A61F 2002/30266* (2013.01); *A61F 2002/30365* (2013.01); *A61F 2002/30397* (2013.01); *A61F 2002/30401* (2013.01); *A61F 2002/30482* (2013.01); *A61F 2002/30484* (2013.01); *A61F 2002/30515* (2013.01);*A61F 2002/30518* (2013.01); *A61F 2002/30543* (2013.01); *A61F 2002/30556* (Continued)

(58) Field of Classification Search
CPC ....... A61F 2/44; A61F 2/4455; A61F 2/4465; A61F 2/447; A61F 2002/4475
See application file for complete search history.

(56) References Cited

U.S. PATENT DOCUMENTS

| | | | |
|---|---|---|---|
| 6,723,128 B2 | 4/2004 | Uk | |
| 8,778,025 B2 * | 7/2014 | Ragab et al. ............... | 623/17.11 |

(Continued)

FOREIGN PATENT DOCUMENTS

| | | |
|---|---|---|
| DE | 10113689 C1 | 8/2002 |
| EP | 1290985 A2 | 3/2003 |
| EP | 1233732 B1 | 5/2006 |

*Primary Examiner* — Nicholas Woodall
(74) *Attorney, Agent, or Firm* — Lempia Summerfield Katz LLC

(57) ABSTRACT

An expandable cage for intercorporal fusion of lumbar vertebrae comprises a main body with two expandable parallel arms. Each arm has a supporting surface pointing outside and configured to contact an adjacent vertebral body, a groove pointing inside and extending along a transverse direction, and a channel pointing inside and extending along a longitudinal direction. An expansion element is instrument actuated and presses the arms apart expanding the cage. The expansion element is between the arms and comprises a cylindrical base body, two opposing radially aligned ribs on the base body, and a rectangular plate. Both the base body and ribs have curved, pair-wise opposed bearing surfaces. Depending on the cage's expansion state, either the base body bearing surfaces or the rib bearing surfaces contact channels provided in the arms, while the plate engages in the grooves of the arms.

23 Claims, 9 Drawing Sheets

(52) U.S. Cl.
CPC ......... (2013.01); *A61F 2002/30624* (2013.01); *A61F 2002/30637* (2013.01); *A61F 2002/30774* (2013.01); *A61F 2002/30777* (2013.01); *A61F 2002/30785* (2013.01); *A61F 2002/30789* (2013.01); *A61F 2002/30822* (2013.01); *A61F 2002/30843* (2013.01); *A61F 2002/30897* (2013.01); *A61F 2002/4475* (2013.01); *A61F 2002/4629* (2013.01)

(56) References Cited

U.S. PATENT DOCUMENTS

| | | | |
|---|---|---|---|
| 2003/0208275 A1* | 11/2003 | Michelson | 623/17.16 |
| 2004/0158324 A1 | 8/2004 | Lange | |
| 2010/0049324 A1 | 2/2010 | Valdevit et al. | |
| 2012/0029637 A1* | 2/2012 | Ragab et al. | 623/17.11 |

* cited by examiner

EXPANDABLE CAGE FOR THE INTERBODY FUSION OF LUMBAR VERTEBRAE

CROSS-REFERENCE TO RELATED APPLICATIONS

This application claims benefit of German patent application 10 2012 023 042.7 filed on Nov. 26, 2012. The full disclosure of this earlier application is incorporated herein by reference.

BACKGROUND OF THE INVENTION

1. Field of the Invention

The present invention relates to a cage for the intercorporal fusion of lumbar vertebrae.

The technical field to which the present invention relates is spinal surgery. To treat people with degenerative changes to the lumbar vertebral column, in which a mono- or multi-segment fusion is indicated, but also in cases which are aimed at a decompression of the neural structures, two operating techniques in particular have proven effective, which enable intervention without additional trans-abdominal access. In the so-called PLIF operating technique (Posterior Lumbar Intervertebral Fusion) two so-called cages are preferably implanted for each disc space by way of posterior access. The implanted cages serve as placeholders in the intervertebral space and restore the spacing of the adjacent vertebral bodies as desired by the surgeon. In addition, the vertebrae are therefore stabilised in a fixed position by a rod-screw system applied posteriorly. The second operating technique, known as TLIF (Transforaminal Lumbar Intervertebral Fusion) is an operating method which has been further developed from the PLIF operating technique. In this procedure, a single cage is implanted via dorsolateral access. Posterior stabilisation is also applied with this technique. The aim of both operating techniques is to achieve a fusion, i.e. an osseous connection, of the affected segments. This can be improved by the addition of a synthetic or a biological bone-substitute material. The cages are normally made from metal or plastic materials.

2. Description of Related Art

For both operating methods, the prior art discloses cages which are approximately trapezoidal or wedge-shaped in longitudinal section with a rectangular cross-section, which cages correct the curvature of the vertebral column as result of their shape. So-called expandable cages of the said type are also already known, and these offer the advantage of enabling relatively easy insertion owing to the low entry height.

EP 1 290 985 B1 discloses an expandable cage of this type which has an expansion element inside it for expanding the cage, wherein a spacer disc, which is movable on slide rails with angled slide surfaces, can be inserted so that, depending on the depth of insertion of the spacer element, the cage expands to varying degrees as far as an end position formed by a projection or a step.

Although this known cage offers the above-mentioned advantage owing to its expandability, the necessary procedure of inserting the spacer disc as far as the end position for expanding the cage is, however, complex and requires a high level of ability and skill on the part of the surgeon. When a cage is only half-expanded, the spacer element is located in the centre of the cage, the front ends protrude and a reliable load transfer is not ensured. Moreover, the spacer disc has to be positively guided to prevent tilting. It remains equally difficult to clearly control the degree of expansion which is achieved and to monitor whether the end position has been reliably reached.

DE 101 13 689 C1 discloses a generic expandable cage which prevents the above-mentioned disadvantages in that the expansion of the cage is effected by a rotatable expansion element mounted at its front end. To this end, this cage has two substantially mutually parallel-extending arms which form supporting surfaces for adjacent vertebral bodies on their outsides and are connected at one end by way of a bridge. At the respective other ends of the arms, there is an intermediate elliptical expansion element, which engages in the ends of the arms and is rotatable about an axis of rotation extending parallel to the arms. This enables the arms to be expanded to a greater or lesser extent depending on the angular position of the expansion element. In the unexpanded state of the cage, the outer surfaces of the expansion element with the smaller radius of curvature rest in oval cutouts in the arms. In the expanded state, the outer surfaces of the expansion element with the larger radius of curvature each lie in depressions in the arms, which are delimited on both sides by small steps. The expansion element can be inserted from the outside into groove-shaped depressions in both arms, so that it can be secured in this manner against displacement in the axial direction.

Although more simple and rapid adjustability of the cage into the expanded position can be achieved in this way, the limited contact surface between the expansion element and the arms in the expanded state means that the load-bearing capacity is low, especially since, when subjected to a load, it is not possible to reliably prevent the expansion element from rotating about the axis of rotation and the arms from tilting about axes lying parallel to the axis of rotation.

U.S. Pat. No. 6,723,128 B2 discloses a monolithically constructed expandable cage having a rotatable expansion element which is incorporated flush between two arms in an insertion opening and whereof the respective contact surfaces supporting the arms are widened and therefore enable a greater load transfer. However, when subjected to a load, it is still possible for the arms to tilt about axes lying parallel to the longitudinal axis of the cage since the width of the contact surfaces, which is transverse to the longitudinal axis of the cage, is relatively small by comparison with the width of the cage. It is also not possible to rule out the expansion element itself tilting about a transverse axis which is perpendicular to the longitudinal axis of the cage. The expansion path is restricted.

EP 1 233 732 B1 discloses an expandable cage with two expandable arms, which are optionally also connected to one another in hinged manner and which have a rotatable expansion element located between them. In a preferred form, the plate-shaped expansion element has a modified rectangular or rhomboidal form with diagonally opposed rounded corners in order to facilitate the rotation of the expansion element when transferring from the unexpanded to the expanded state of the cage and to prevent a substantial over-distraction of the adjacent vertebral bodies during this procedure. The expansion element is held and guided in guides of the two expandable arms. Although it is also possible here for the expansion element to tilt about a transverse axis which is perpendicular to the longitudinal axis of the cage, a tilting of the arms about an axis lying parallel to the longitudinal axis of the cage is prevented by complex stabilising partial wall structures of the arms themselves. These not only increase the rigidity of the arms but are at the same time also restrictive in terms of allowing the largest possible lateral recesses in the cage, which are advantageous for improved radiological penetration.

SUMMARY OF THE INVENTION

It is an object of the present invention to provide an expandable cage for the intercorporal fusion of lumbar vertebrae, which can be brought into its expanded state simply and in little time and which at the same time ensures a high and reliable load transfer.

This object is achieved by an expandable cage for the intercorporal fusion of lumbar vertebrae comprising an elongated main body that comprises two expandable arms that extend in an at least substantially parallel fashion to each other. Each arm has a supporting surface pointing outside and configured to contact an adjacent vertebral body, a groove pointing inside and extending along a transverse direction of the main body, and a channel pointing inside and extending along a longitudinal direction of the main body. The main body further comprises a bridge-like connection section connecting the arms so that, in a medial longitudinal section, the main body has at least substantially a U-shaped profile and the arms have two free ends. The bridge-like connection section has an opening that is configured to receive an instrument for expanding the cage. The main body further comprises an expansion element that is configured to press, if the expansion element is actuated by the instrument, the arms apart thereby expanding the cage. The expansion element is located at the free ends of the arms and is rotatably mounted between the arms. It comprises an elongated base body, two opposing radially aligned ribs attached to the base body and extending along the longitudinal direction of the main body, and a rectangular plate. The latter is connected to the base body, has rounded edges and has short sides that engage in the grooves provided in the arms both in the unexpanded and expanded state of the cage. The expansion element further comprises a driving device that is located at a rear side of the expansion element, points towards the bridge-like connection and is configured to establish a releasable connection to the instrument. Both the base body and the ribs have curved, pair-wise opposed bearing surfaces. Depending on the expansion state of the cage, either the bearing surfaces of the base body or the bearing surfaces of the ribs contact the channels provided in the arms.

In addition to the rapid adjustability of the cage, which requires a simple rotation through 90° by means of a suitable instrument in order to arrive from the unexpanded into the expanded state and vice versa, a particular advantage consists in that, in both states relatively extensive elongated mutually orthogonal contact surfaces between the expansion element and the arms supporting the vertebral bodies are present, which ensures not only a high load transfer, but prevent at the same time a tilting of the expansion element under a load. Displacements of the expansion element in the longitudinal direction and in the transverse direction with respect to the cage are likewise prevented in both states.

Further advantages may be realised by the options for driving the expansion element from the posterior and anterior, in which case it is expediently possible for the latter to be available as an emergency drive for revision surgery. For improved radiological investigation, the cage may have open side walls.

The driving device may be configured to establish a multi-tooth connection to the instrument, and in particular the driving device may comprise a hexalobular socket.

The expansion element may comprise a further driving device that is located at a front side of the expansion element, points away from the bridge-like connection and is configured to establish a releasable connection to a revision tool, wherein the further driving element has a central bore passing through the base body and two grooves that project from the bore, extend in the direction of the ribs and have a width that is smaller than a diameter of the bore. The grooves provided in the arms may have base surfaces on which, in the expanded stat of the cage, the short sides of the rectangular plate rest.

Bead-shaped recesses may be formed centrally in the short sides of the rectangular plate, and complementary raised portions may be formed centrally in the base surfaces of the grooves. This configuration results in an advantageous additional locking of the cage in the expanded state.

The plate may have a lateral notch that is configured to enable a precise position control of the expansion element in the cage using an imaging technique. This enables advantageous position control of the expansion element in the cage, independently of an adjusting instrument, by means of an imaging procedure.

The arms may comprise lateral hooks that are configured to prevent the expansion element from springing out into a faulty position.

The opening in the bridge-like connection may comprise a first cylindrical section having a smooth surface and a second cylindrical section having a threaded surface. As a result of this a reliable attachment to an instrument is achieved, and an opening for introducing synthetic osseous matter is produced at the same time.

The bridge-like connection may be constructed in one piece with the arms so that the main body is monolithic. The monolithic construction of the main body of the cage enables simplified manufacture. The resultant need for the presence of flexible expandable arms, which can be achieved by relatively thin deformable arm regions, for example by means of oval moulded portions, results in lateral sides which are open to the greatest extent possible and enable improved radiological penetration.

The bridge-like connection may comprise one or two hinge-like joints formed between the arms. This results in a relatively low deflection of the arms in the case of differing load-introduction situations.

The supporting surface of each arm may have a curvature along the longitudinal direction of the main body and a lead-in chamfer at the free end of the arm. The supporting surface of each arm may then be provided with teeth configured to anchor the cage in the adjacent vertebral bodies. As a result of this configuration an improved adaptation to the shape of the vertebral body is attained, simpler insertion of the cage is achieved and a primary anchoring is effected.

Each arm may have, in a plan view, the shape of a parallelogram, of a rectangle or of a quadrilateral having sides of different lengths and two right-angles. These basic shapes result in expedient configurations for the said varying operating techniques.

Openings in the arms provide an option for bone penetration as a means of secondary anchoring.

Different shapes of vertical openings, which are adapted to different bending loads of the arms, enable maximum bone penetrations to be optionally achieved. For example, each arm may be provided with an opening that becomes smaller towards the bridge-like connection, or with a plurality of openings having the shape of slots that are arranged in mutually parallel fashion, or with openings having the shape of a rectangle.

All outer corners and edges of the expansion element may be blunted or provided with a radius. This results in an expedient construction of the cage.

BRIEF DESCRIPTION OF THE DRAWINGS

Various features and advantages of the present invention may be more readily understood with reference to the following detailed description taken in conjunction with the accompanying drawing in which.

DESCRIPTION OF PREFERRED EMBODIMENTS

Figure 1:
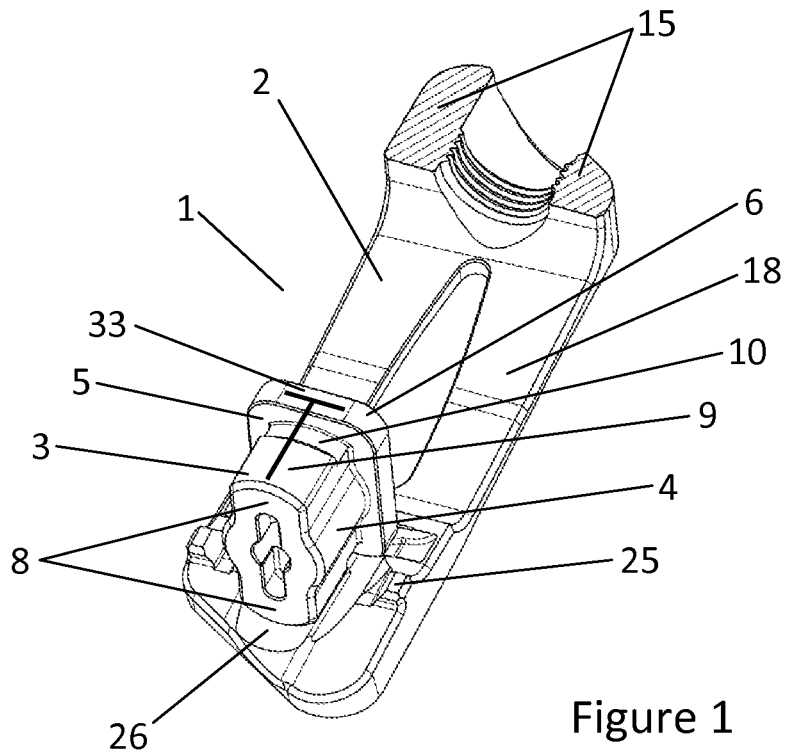
FIG. 1 a horizontal medial longitudinal section through the monolithic main body of a cage according to the invention with an expansion element inserted in an expanded position on the lower arm.

FIG. 1 shows a horizontal medial longitudinal section through the monolithic main body (2) of a cage (1) according to the invention, with an expansion element (3) inserted in an expanded position on the lower arm (18). The expansion element (3) has a rotatable elongated cylindrical base body (4) on the rear end of which a rectangular plate (5) having rounded edges (6) extending in the longitudinal direction of the cage (1) is integrally formed in one piece. Two one-piece opposing ribs (8), whereof the respective radial bearing surfaces (9) terminate at the shorter narrow sides (33) of the rectangular plate (5), are constructed from the plate (5) as far as the front end of the base body (4) of the expansion element (3). The width of the ribs (8) almost reaches the diameter of the cylindrical base body (4). Respective rectangular grooves (10) are incorporated in the ribs (8) so that they extend parallel to the shorter narrow side (33) of the rectangular plate (5) and a lateral surface coincides with the front top surface of the plate (5). In the expanded position of the expansion element (3), the curved bearing surfaces (9), which are opposed to one another in pairs, extend in channels (26) which extend in the longitudinal direction of the cage (1) and are present on the insides of the arms (18). In the rear part of the base body (4), the expansion element (3) has a hexalobular socket (12) (FIG. 4) which is accessible from the posterior and serves for rotating the expansion element (3).

Figure 2:
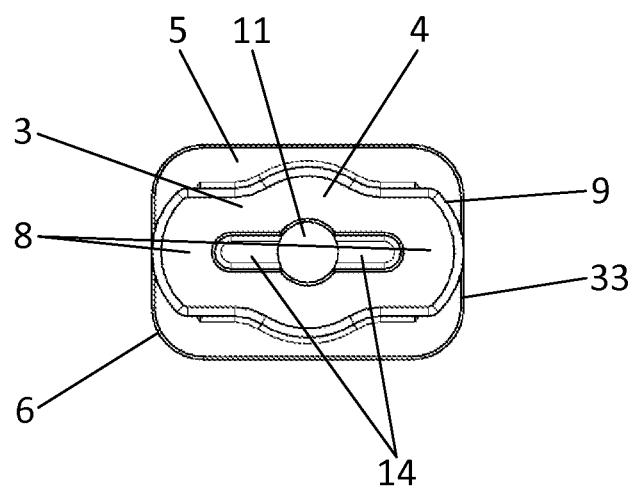
FIG. 2 the front view of the expansion element according to FIG. 1.

As shown in FIG. 2, the expansion element (3) has a central bore (11). For improved revision, two grooves (14) are incorporated in the front surface of the expansion element (3), which grooves extend in the direction of the ribs (8), end a short distance before the bearing surface (9) and have a width which is smaller than the diameter of the bore (11). The grooves are not continuous through the body, i.e. their depth is restricted.

Figure 3:
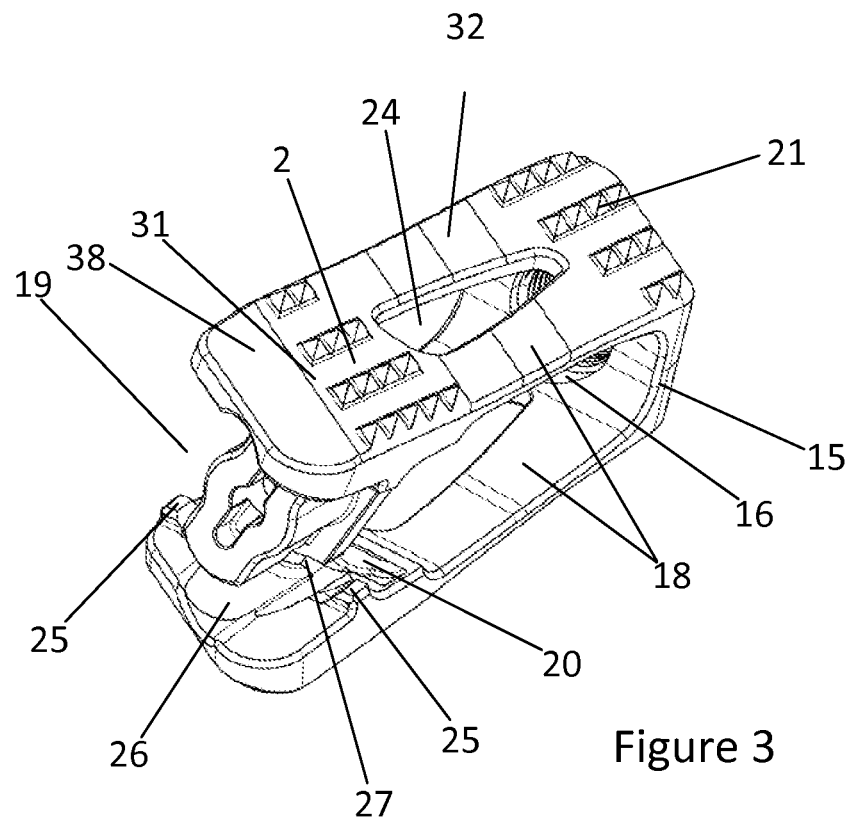
FIG. 3 the cage of FIG. 1 in a partially expanded state.
Figure 4:
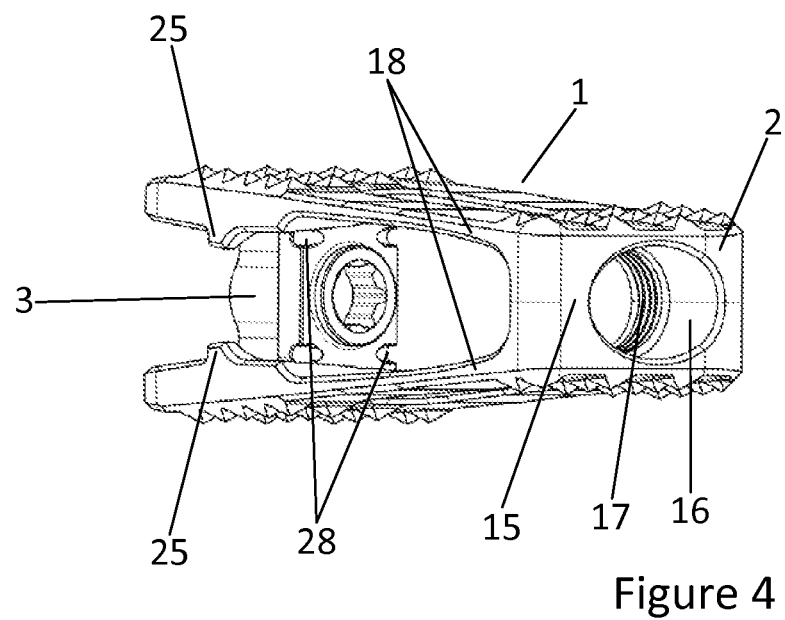
FIG. 4 the cage of FIG. 3 in the expanded state.
Figure 11:
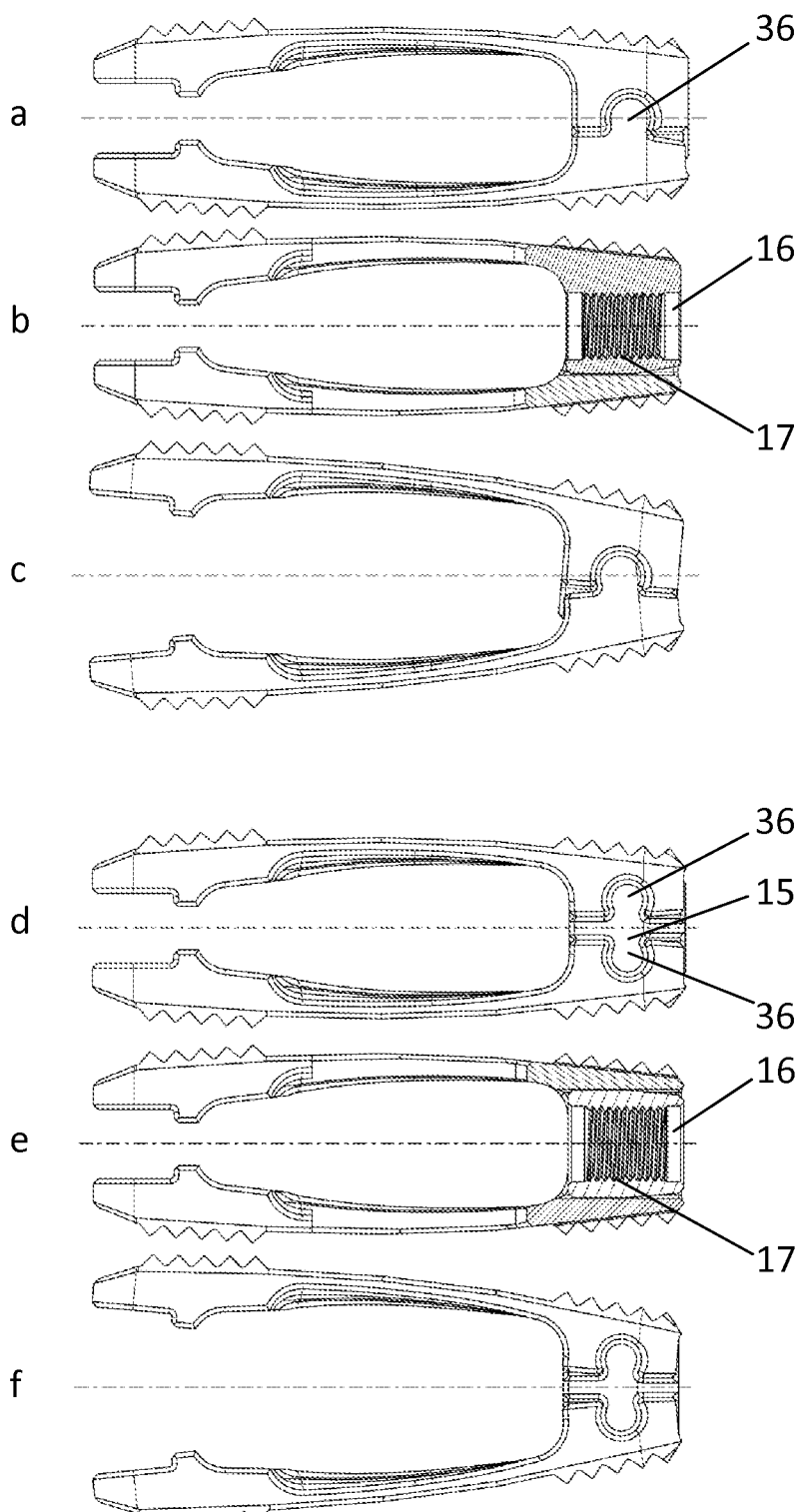
FIGS. 11a-11f cages with one or two hinge-like joints.

As can be seen in FIG. 3, and particularly in FIG. 4, the main body (2) of the cage (1) has a substantially U-shaped profile in medial longitudinal section, with its anterior end being open. Two approximately mutually parallel-extending expandable arms (18), which each serve as supporting surfaces (32) for adjacent vertebral bodies, are connected to one another by way of a bridge-like connection (15). In the example shown, the bridge-like connection (15) is a direct connection formed in one piece with the arms (18) to produce a monolithic main body (2). However, it is alternatively possible for the two arms (18) to be connected to one another with one or two hinge-like joints (36) by way of bridge-like connections, as shown in FIG. 11.

Figure 6:
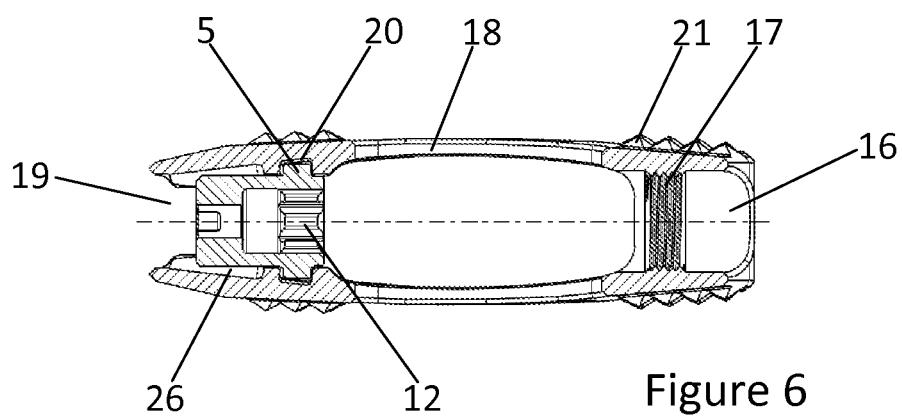
FIG. 6 a vertical medial longitudinal section through the cage of FIG. 4 in the unexpanded state.

The connection (15) has a central opening (16) for inserting instruments. This opening (16) is formed cylindrically at the rear end in order to then merge into a screw thread (17, FIG. 4). The thickness of the arms (18) decreases towards the centre to produce an elliptical opening in medial longitudinal section. At the front end, the arms (18) are increased until a gap (19) formed by them has an opening size which corresponds to the width of the ribs (8) when the cage (1) is not expanded (FIG. 6). In the increased ends of the arms (18), as seen from the gap (19), there are opposing grooves (20) in which the plate (5) engages such that the expansion element (3) is fixed in the longitudinal direction of the cage (1). Cylindrical channels (26), whereof the radius is equal to the bearing surfaces (9) of the ribs (8) of the base body (4), are incorporated centrally in the increased ends of the arms (18). The length of the channels (26) in medial longitudinal section is dimensioned so that a web (27) remains such that it engages in the groove (10) of the expansion element (3) and is in contact with the plate (5).

In the unexpanded state of the cage (1), the ribs (8) lie transversally and the main body (2) is not expanded. The cylindrical lateral surface of the base body (4) lies extensively in the channels (26) of the thickened ends of the arms (18). The outsides (31) of the arms (18), which are constructed as supporting surfaces (32), are provided with a profiling (21) (FIG. 3).

FIG. 4 shows the cage (1) with the main body (2) and expansion element (3) as seen from the posterior side in the expanded state. Lateral notches (28) are clearly shown in the expansion element (3), which can be used for radiological position control. The opening (16) and the screw thread (17) are also shown.

Since the connection (15) merges in one piece into the arms (18), this construction enables the lateral recess to be as large as possible owing to the open sides of the cage (1), which extend in the longitudinal direction, since this ensures the best possible radiological penetration. A deformability of the arms (18) during expansion is necessary. The deformability is further promoted by the geometrical design of the arms (18).

Small hooks (25), which prevent the expansion element (3) from springing out into a faulty position, are constructed at the side of the increased ends of the arms (18).

Figure 5:
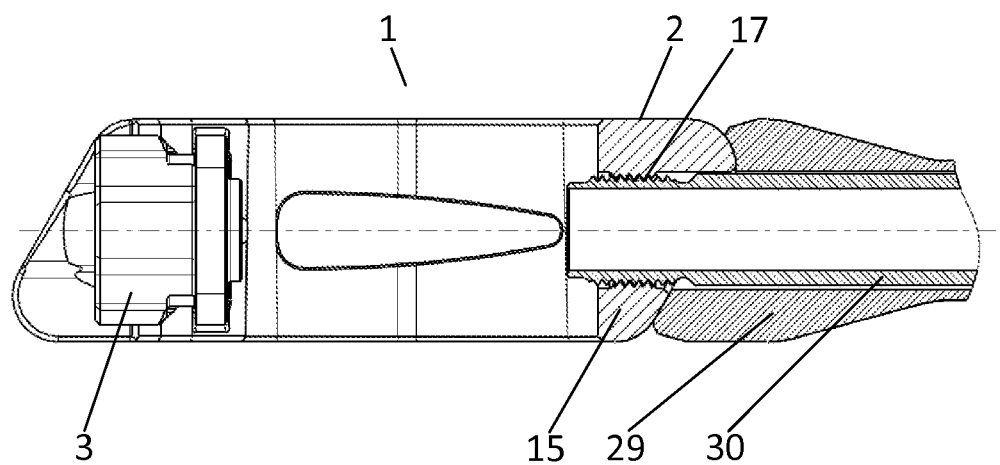
FIG. 5 a horizontal medial longitudinal section through the cage of FIG. 4 with a connected instrument.

The attachment of an instrument (29) to the cage (1) or the connection (15) is shown in FIG. 5 and is designed such that no additional recess is required in the cage (1). To this end, a tube (30) is screwed into the screw thread (17) in order to connect the instrument (29) to the cage (1) in torsion-resistant manner, with the obliquely extending connection (15) being advantageous for preventing torsion. The tube (30) can also be used to introduce preferably synthetic osseous matter into the cage (1).

FIG. 6 shows the unexpanded cage (1) in medial vertical longitudinal section, as it is incorporated between the vertebral bodies. The bearing surfaces (9) of the base body (4) lie in the respective channels (26). The plate (5) engages with its longer narrow side (33) in the groove (20). By means of a suitable tool (not illustrated) with a hexalobe at its tip, which can be inserted into the hexalobular socket (12), the expansion element (3) only has to be rotated through 90° in order to move the cage (1) into the expanded state. The embodiment enables both directions of rotation so that the expansion is reversed by both a reverse rotation through 90° and a further rotation through 90°.

Figure 7:
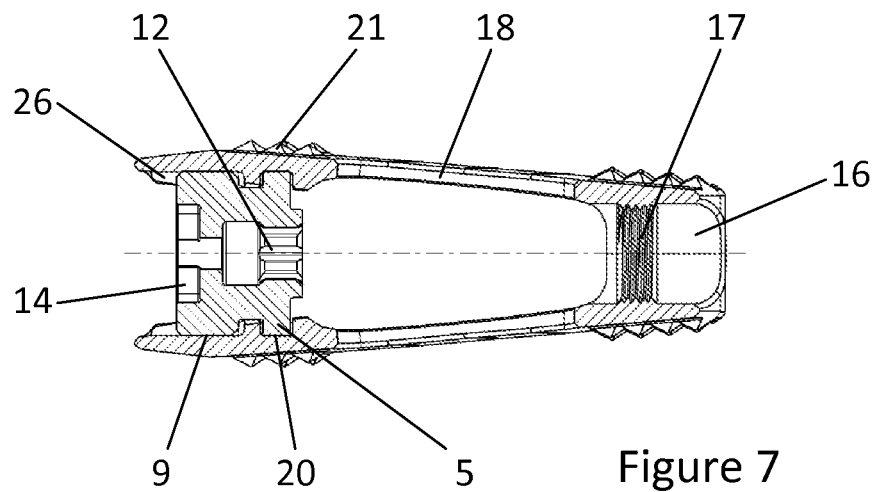
FIG. 7 a vertical medial longitudinal section through the cage of FIG. 4 in the expanded state.

FIG. 7 shows the expanded cage (1) in medial vertical longitudinal section. In this position, the curved bearing surfaces (9) of the ribs are in extensive contact with the channels (26) and, at the same time, the plate (5) lies with its shorter narrow sides (33) flat in the grooves (20). This ensures a reliable non-tilting load transfer with the greatest possible bearing surface in a T-shape (cf. FIG. 1). FIG. 7 also further shows the grooves (14) in which a suitable tool can engage to remove the expansion element (3) from the anterior when necessary during a revision OP. A rear device (12) for rotatably driving the expansion element (3) is likewise shown.

Figure 8:
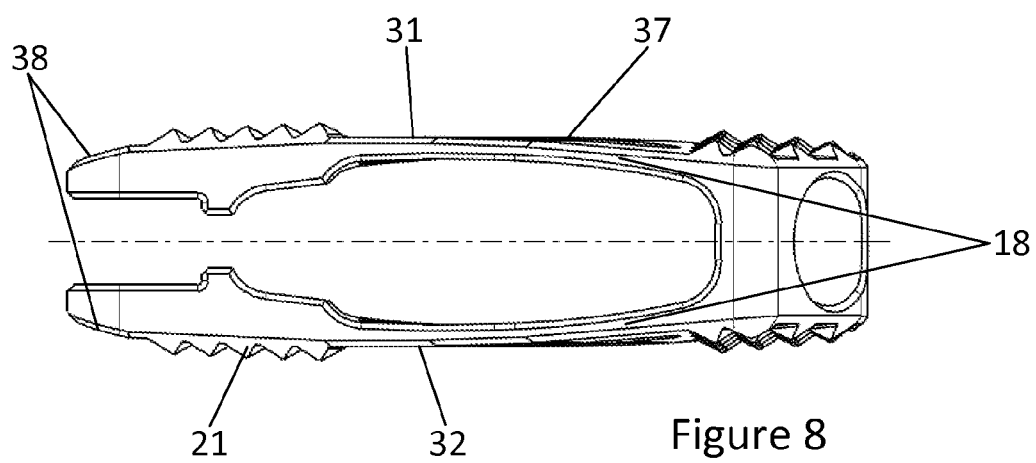
FIG. 8 the main body of the cage of FIG. 4 in a lateral unexpanded view.

FIG. 8 shows the inventive main body (2) of the cage (1) according to FIG. 4 in a lateral unexpanded view. The outsides (31) of the arms (18), which form the supporting surfaces (32), are curved slightly in the longitudinal direction of the cage (1). A lead-in chamfer (38) is also shown in each case at the front ends of the arms (18). Teeth (21) are located in the front and in the rear region of the supporting surfaces (32) for the purpose of primary anchoring.

Figure 9:
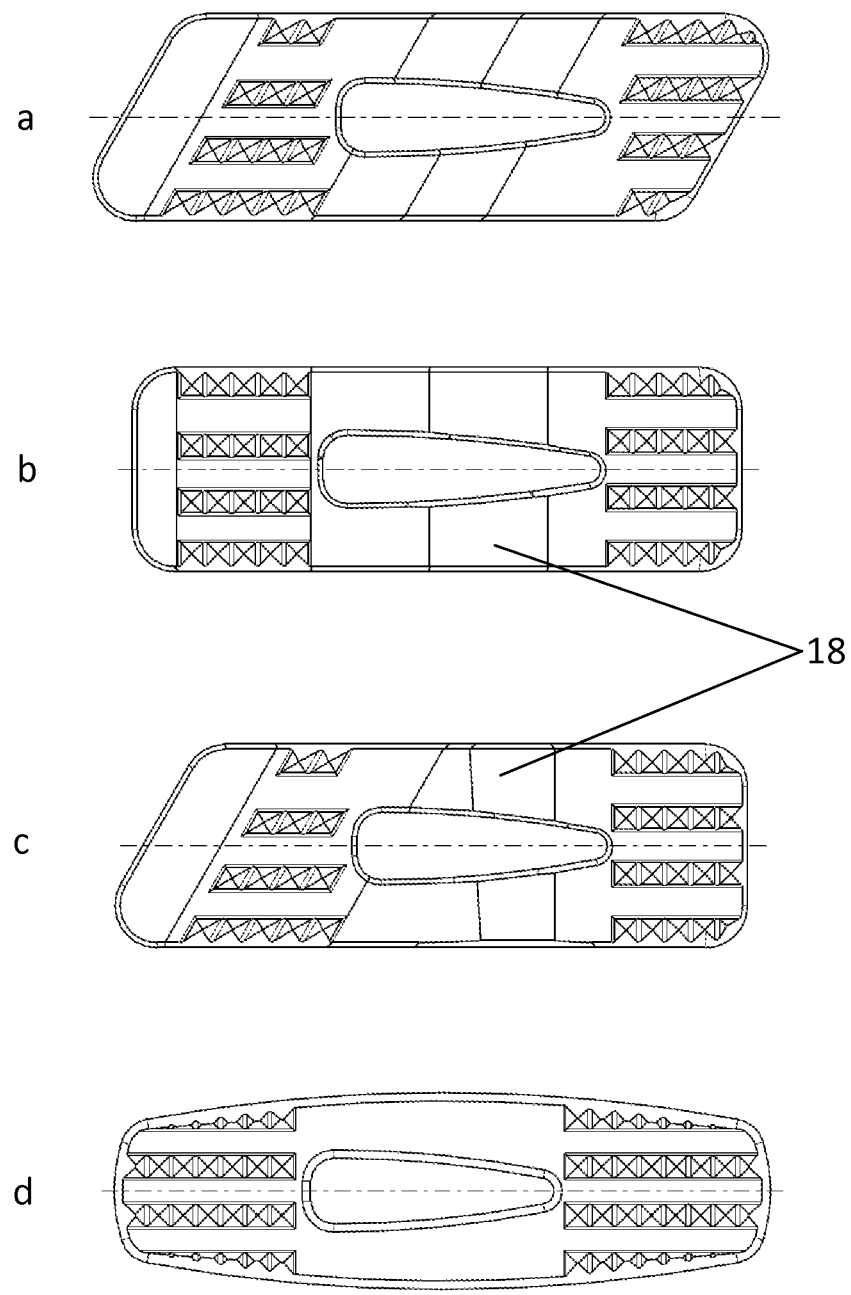
FIGS. 9a-9d different basic shapes of the cage according to alternative embodiments of the invention in a plan view.

FIG. 9a-d show various basic shapes of cages (1) according to the invention in plan view. FIG. 9a shows for example a basic shape in the form of a parallelogram. In a transforaminal operating technique, with angled insertion and positioning, it ensures improved load transfer since the cage (1) terminates approximately at the edge region of the vertebral body. FIG. 9b shows a possible rectangular basic shape. FIG. 9c shows that the basic shape can also be a polygon with sides of different length, with two right-angles present on a short side. FIG. 9d shows a predominantly elliptical basic shape of the arms (18), which facilitate low-invasive intervention, particularly when inserting the cage. The various options for arranging the teeth (21) on the arms (18) are also shown.

Figure 10:
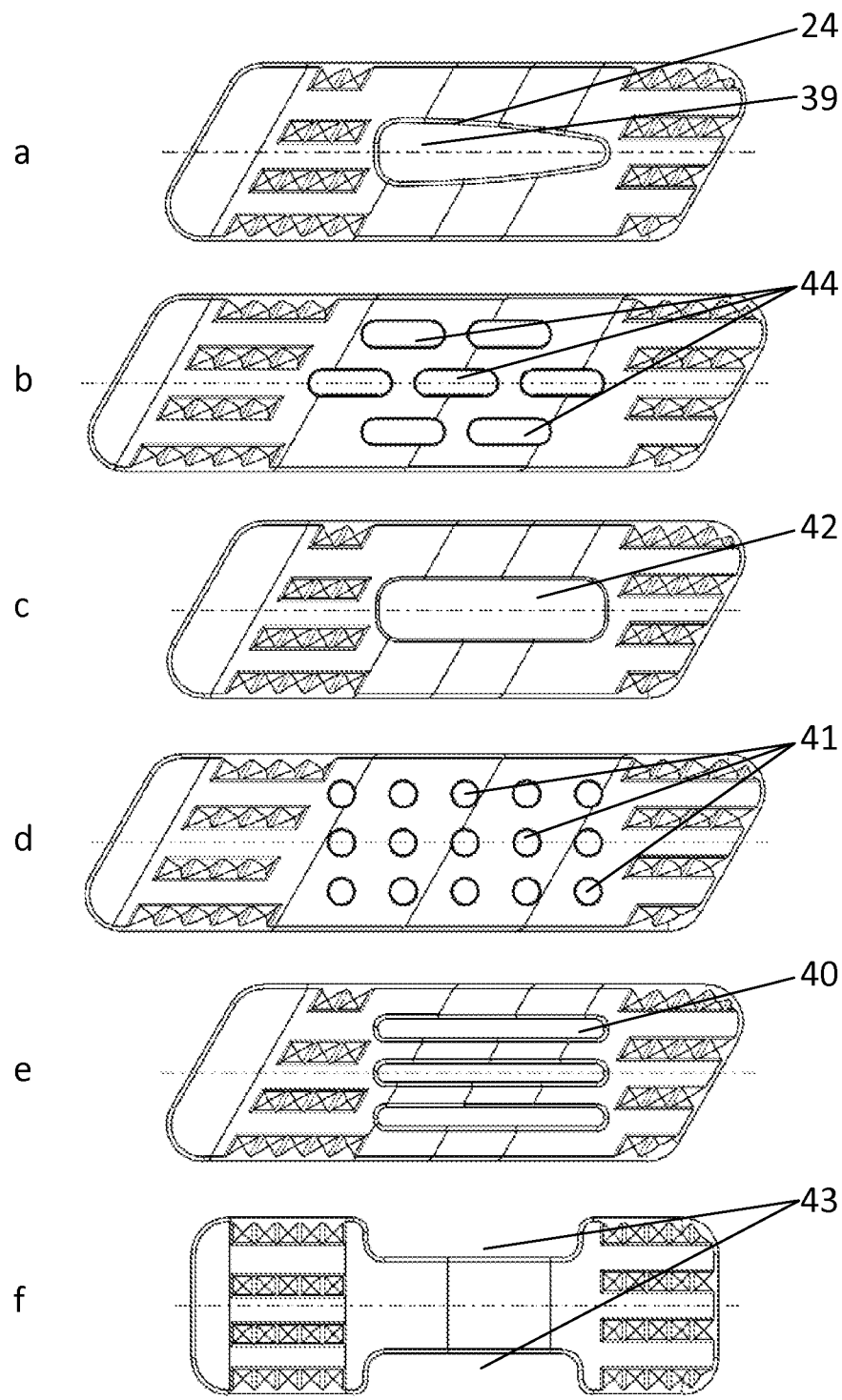
FIGS. 10a-10f different forms of vertical recess.

FIGS. 10a-f show various forms of vertical recess (24) in the arms (18) for fusing with osseous matter as a secondary anchoring. In FIG. 10a, a recess (24) is constructed as a window (39) which becomes smaller towards the posterior in substantially partially elliptical form. In FIG. 10b, recesses (24) in the form of slots (44) are present, which extend in mutually parallel-extending rows with two or three slots per row. The vertical recesses (24) can also be constructed as a substantially rectangular window (42), as shown in FIG. 10c. FIG. 10d shows a form of the recesses (24) which comprise successive bores (41) arranged matrix-like in the longitudinal direction of the cage (1) in a plurality of mutually parallel-extending rows. The recess (24) can consist of three narrow through-holes (40) of equal length extending mutually parallel in the longitudinal direction of the cage (1), as shown in FIG. 10e. FIG. 10f shows vertical recesses (24) comprising lateral cutouts (43) in pairs on the longitudinal sides of the arms (18).

FIGS. 11a-c and 11d-f show cages (1) with one or two hinge-like joints (36) which each comprise two rotatable connections mounted laterally with respect to the opening (16). FIG. 11a shows a cage (1) with a hinge-like joint (36) in the unexpanded state. FIG. 11b shows this cage (1) in a partial section of the connection (15), which is present between the rotatable connections of the hinge-like joint (36). The opening (16) and the screw thread (17) for connecting instruments to the cage (1) are clearly shown. FIG. 11c shows this cage (1) in the expanded state. The connection (15) here is advantageously converted into the joint (36). FIG. 11d shows a cage (1) with two hinge-like joints (36) in the unexpanded state. FIG. 11e shows this cage (1) in a partial section of the connection (15) which is present between the rotatable connections of the joints (36). The opening (16) and the screw thread (17) are likewise clearly shown. FIG. 11f shows this cage (1) in the expanded state. The connection (15) here advantageously forms the common basis for the vertically superimposed rotatable connections of the two joints (36). Both variants are advantageous over a monolithic design of the main body in that there is less deformation of the arms (18) during the expansion.

FIGS. 12a-g show various expansion elements (3) within the scope of the invention, which have devices for the rotatable drive in both the rear and the front part.

Figure 12:
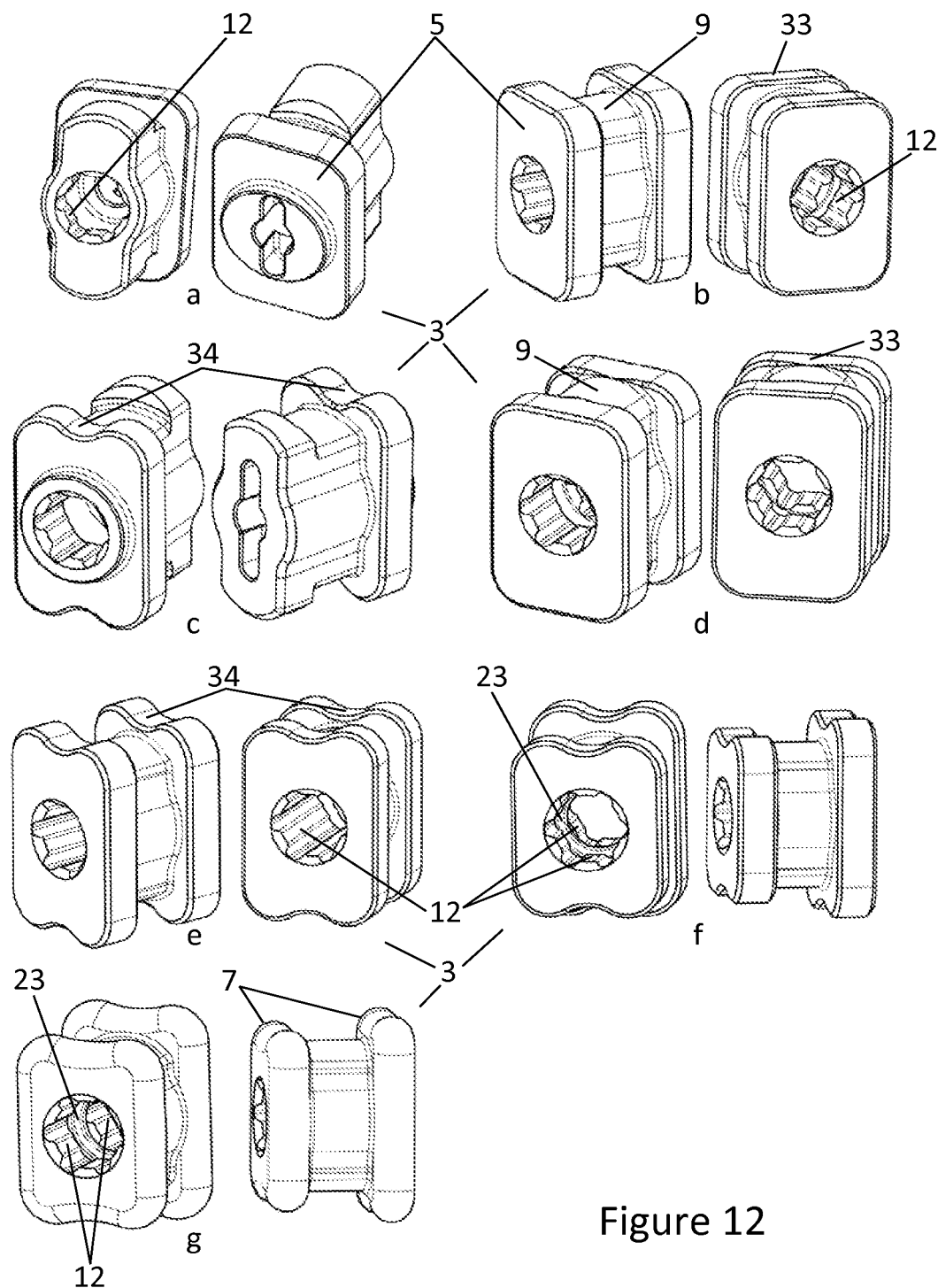
FIGS. 12a-12g different embodiments of expansion elements.

FIG. 12a shows an expansion element (3) as shown for example in the illustration of FIG. 1, although the devices for rotatably driving the cage (1) are changed here.

The expansion element (3) in FIG. 12b is notable for two rectangular plates (5) at both ends of the elongated base body (4), which have the same dimensions. The bearing surfaces (9) do not terminate at the surfaces of the shorter narrow sides (33). A hexalobular socket (12) is incorporated in each plate (5).

The expansion element (3) according to FIG. 12c is notable for bead-shaped recesses (34) in the shorter narrow sides (33) of the rectangular plate (5) for improved locking in the expanded state of the cage.

FIG. 12d shows an expansion element (3) with two plates (5) of equal dimensions, wherein the bearing surface (9) terminates at the surfaces of the shorter narrow sides (33) to produce an H-shaped bearing lying flat in a plane.

The expansion element (3) according to FIG. 12e differs from the expansion element according to FIG. 12b in that additional bead-shaped recesses (34) serving for improved locking are incorporated in both shorter narrow sides (33) of the plates (5), whereof the depth reaches as far as the height of the bearing surfaces (9).

FIG. 12f shows a similar expansion element (3) to that of FIG. 12e, with the difference being that one of the plates (5) projects beyond the other in height and width.

FIG. 12g shows an expansion element (3) in which all outer corners and edges of the expansion element (3) are blunted or provided with a radius.

FIGS. 12f and 12g show, both in the rear and also in the front part of the expansion elements (3), hexalobular sockets (12) between which a respective collar (23) is shown, which also serves to safeguard against internal breakdown.

FIG. 12e shows an expansion element (3) in which the hexalobular socket (12) is of a continuous construction from the front to the rear part.

All the embodiments shown also advantageously ensure that the corresponding cage (1) is locked reliably and against tilting in the expanded state, in which case it goes without saying that the thickened ends of the arms (18) are each adapted to an expansion element (3) according to FIGS. 12a-g. The position is reliably fixed in each case by means of the grooves (20) and channels (26) which are arranged crosswise.

LIST OF REFERENCE NUMERALS

1 Cage
2 Main body
3 Expansion element
4 Base body
5 Plates
6 Edges
7 Radius
8 Ribs
9 Bearing surfaces 10 Grooves
11 Bore
12 Hexalobular socket
13 (free)
14 Grooves
15 Connection
16 Opening
17 Screw thread
18 Arms
19 Gap
20 Grooves
21 Teeth
22 Supporting surface
23 Collar
24 Recess
25 Hooks
26 Channel
27 Web
28 Notches
29 Instrument
30 Tube
31 Outsides of the arms
32 Supporting surface
33 Narrow sides of the plates
34 Bead-shaped recesses
36 Hinge-like joints
37 Curvature
38 Lead-in chamfer
39 Partially elliptical window
40 Through-hole
41 Bores
42 Rectangular window
43 Lateral cutouts
44 Slots

The invention claimed is:

1. An expandable cage for the intercorporal fusion of lumbar vertebrae, comprising
an elongated main body that comprises
two expandable arms that extend in an at least substantially parallel fashion to each other, wherein each arm has
a supporting surface pointing outside and configured to contact an adjacent vertebral body,
a groove pointing inside and extending along a transverse direction of the main body, and
a channel pointing inside and extending along a longitudinal direction of the main body,
a bridge-like connection section connecting the arms so that, in a medial longitudinal section, the main body has at least substantially a U-shaped profile and the arms have two free ends, wherein the bridge-like connection section has an opening that is configured to receive an instrument for expanding the cage;
an expansion element that is configured to press, if the expansion element is actuated by the instrument, the arms apart thereby expanding the cage, wherein the expansion element
is located at the free ends of the arms and is rotatably mounted between the arms,
comprises an elongated base body, two opposing radially aligned ribs attached to the base body and extending along the longitudinal direction of the main body, and a rectangular plate that
is connected to the base body,
has rounded edges and
has short sides that engage in the grooves provided in the arms both in the unexpanded and expanded state of the cage,
wherein the expansion element further comprises a driving device that is located at a rear side of the expansion element, points towards the bridge-like connection and is configured to establish a releasable connection to the instrument,
wherein both the base body and the ribs have curved, pair-wise opposed bearing surfaces, and wherein, depending on the expansion state of the cage, either the bearing surfaces of the base body or the bearing surfaces of the ribs contact the channels provided in the arms.

2. The cage of claim 1, wherein the base body has a cylindrical shape.

3. The cage of claim 1, wherein the driving device is configured to establish a multi-tooth connection to the instrument.

4. The cage of claim 3, wherein the driving device comprises a hexalobular socket.

5. The cage of claim 1, the expansion element comprises a further driving device that is located at a front side of the expansion element, points away from the bridge-like connection and is configured to establish a releasable connection to a revision tool, wherein the further driving element has a central bore passing through the base body and two grooves that project from the bore, extend in the direction of the ribs and have a width that is smaller than a diameter of the bore.

6. The cage of claim 1, wherein the grooves provided in the arms have base surfaces on which, in the expanded stat of the cage, the short sides of the rectangular plate rest.

7. The cage of claim 6, wherein bead-shaped recesses are formed centrally in the short sides of the rectangular plate, and wherein complementary raised portions are formed centrally in the base surfaces of the grooves.

8. The cage of claim 1, wherein the plate has a lateral notch that is configured to enable a precise position control of the expansion element in the cage using an imaging technique.

9. The cage of claim 1, wherein the arms comprise lateral hooks that are configured to prevent the expansion element from springing out into a faulty position.

10. The cage of claim 1, wherein the opening in the bridge-like connection comprises a first cylindrical section having a smooth surface and a second cylindrical section having a threaded surface.

11. The cage of claim 1, wherein the bridge-like connection is constructed in one piece with the arms so that the main body is monolithic.

12. The cage of claim 1, wherein the bridge-like connection comprises a hinge-like joint formed between the arms.

13. The cage of claim 12, wherein the bridge-like connection comprises two hinge-like joints formed between the arms.

14. The cage of claim 1, wherein the supporting surface of each arm has a curvature along the longitudinal direction of the main body and a lead-in chamfer at the free end of the arm, and wherein the supporting surface of each arm is provided with teeth configured to anchor the cage in the adjacent vertebral bodies.

15. The cage of claim 1, wherein each arm has, in a plan view, the shape of a parallelogram.

16. The cage of claim 15, wherein each arm has, in a plan view, the shape of a rectangle.

17. The cage of claim 1, wherein each arm has, in a plan view, the shape of a'quadrilateral having sides of different lengths and two right-angles.

18. The cage of claim 1, wherein each arm has, in a plan view, the shape of an ellipse.

19. The cage of claim 1, wherein each arm is provided with an opening that becomes smaller towards the bridge-like connection.

20. The cage of claim 1, wherein each arm is provided with a plurality of openings having the shape of slots that are arranged in mutually parallel fashion.

21. The cage of claim 1, wherein each arm is provided with a plurality of openings having the shape of a rectangle.

22. The cage of claim 1, wherein each arm is provided with a plurality of openings having the shape of bores.

23. The cage of claim 1, wherein all outer corners and edges of the expansion element are blunted or provided with a radius.

\* \* \* \* \*